(12) United States Patent
Masui et al.

(10) Patent No.: US 9,522,105 B2
(45) Date of Patent: Dec. 20, 2016

(54) SKIN CLEANSING COMPOSITION

(75) Inventors: Takashi Masui, Chiba (JP); Hiroki Takeuchi, Bunkyo-ku (JP)

(73) Assignee: KAO CORPORATION, Tokyo (JP)

( * ) Notice: Subject to any disclaimer, the term of this patent is extended or adjusted under 35 U.S.C. 154(b) by 162 days.

(21) Appl. No.: 14/342,290

(22) PCT Filed: Aug. 30, 2012

(86) PCT No.: PCT/JP2012/072017
§ 371 (c)(1),
(2), (4) Date: Feb. 28, 2014

(87) PCT Pub. No.: WO2013/031898
PCT Pub. Date: Mar. 7, 2013

(65) Prior Publication Data
US 2014/0202484 A1    Jul. 24, 2014

(30) Foreign Application Priority Data
Sep. 2, 2011 (JP) ................................. 2011-191785

(51) Int. Cl.
A61K 8/46 (2006.01)
A61K 8/44 (2006.01)
A61K 8/37 (2006.01)
A61Q 19/10 (2006.01)
A61K 8/36 (2006.01)
A61K 8/39 (2006.01)

(52) U.S. Cl.
CPC ................. A61K 8/466 (2013.01); A61K 8/36 (2013.01); A61K 8/37 (2013.01); A61K 8/39 (2013.01); A61K 8/44 (2013.01); A61K 8/463 (2013.01); A61Q 19/10 (2013.01)

(58) Field of Classification Search
CPC ............ A61K 8/39; A61K 8/36; A61K 8/463; A61K 8/44; A61K 8/466; A61K 8/37; A61Q 19/10
See application file for complete search history.

(56) References Cited

U.S. PATENT DOCUMENTS

| 2006/0233733 A1 | 10/2006 | Beauquey et al. |
| 2007/0062659 A1 | 3/2007 | Sherman et al. |
| 2007/0066500 A1 | 3/2007 | Yang et al. |
| 2008/0261845 A1 | 10/2008 | Yamamoto et al. |
| 2013/0149276 A1 | 6/2013 | Takeuchi et al. |

FOREIGN PATENT DOCUMENTS

| CN | 101288631 A | 10/2008 |
| EP | 0 417 501 A1 | 3/1991 |
| EP | 1 982 692 A2 | 10/2008 |
| EP | 2 612 652 A1 | 7/2013 |
| JP | 61 21199 | 1/1986 |
| JP | 2 175799 | 7/1990 |
| JP | 03 103500 | 4/1991 |
| JP | 08 283974 | 10/1996 |
| JP | 10 110187 | 4/1998 |
| JP | 2001 207189 | 7/2001 |
| JP | 2006 282662 | 10/2006 |
| JP | 2007 112984 | 5/2007 |
| JP | 2008 285479 | 11/2008 |
| WO | 97 01328 | 1/1997 |
| WO | 2012 029950 | 3/2012 |

OTHER PUBLICATIONS

Extended European Search Report issued on Feb. 20, 2015 in Application No. 12827980.9.
U.S. Appl. No. 14/342,405, filed Mar. 3, 2014, Masui, et al.
English translation of the International Preliminary Report on Patentability and Written Opinion issued Mar. 13, 2014 in PCT/JP2012/072017, filed Aug. 30, 2012.
International Search Report Issued Dec. 4, 2012 in PCT/JP12/072017 Filed Aug. 30, 3012.

Primary Examiner — Suzanne Ziska
Assistant Examiner — Thurman Wheeler
(74) Attorney, Agent, or Firm — Oblon, McClelland, Maier & Neustadt, L.L.P.

(57) ABSTRACT

A skin cleansing composition, comprising
(A) an alkyl ether carboxylic acid or a salt thereof represented by formula (1):
wherein, $R^1$ represents an alkyl group having 8 to 18 carbon atoms, n represents a number of from 0 to 20, and M represents a hydrogen atom, alkali metal, alkaline earth metal, ammonium, or organic ammonium,
wherein, $R^1$ has an average carbon number of from 10.8 to 12.8 and the average value of n is from 2.5 to 3.4,
and wherein, the alkyl ether carboxylic acid or a salt thereof contains a component in which n=0 in an amount of from 9.9 to 27% by mass, and contains a component in which n=1 and a component in which n=2 in a total amount of less than 40% by mass, and
(B) an alkyl sulfate or polyoxyethylene alkyl sulfate represented by formula (2):
wherein, $R^2$ represents an alkyl group or an alkenyl group having 8 to 22 carbon atoms, m represents a number of from 0 to 20 and the average of m is less than 2, and Y represents a hydrogen atom or a cation selected from alkali metal, alkaline earth metal, ammonium, alkyl ammonium, alkanol ammonium, and glucammonium.

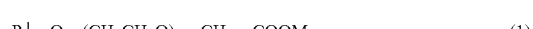

$R^1$—O—$(CH_2CH_2O)_n$—$CH_2$—COOM     (1)

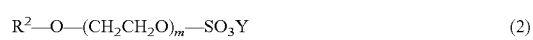

$R^2$—O—$(CH_2CH_2O)_m$—$SO_3Y$     (2)

10 Claims, No Drawings

SKIN CLEANSING COMPOSITION

FIELD OF THE INVENTION

The present invention relates to a skin cleansing composition.

BACKGROUND OF THE INVENTION

Conventionally, in skin cleansing agents, alkyl sulfate, polyoxyethylene alkyl sulfate, or the like has been used as a primary cleansing base, mainly in the U.S. and Europe. However, problems of these skin cleansing agents are sliminess during rinsing and leaving a tight feeling after use (Patent Publications 1 and 2). Also, since the foam produced with these skin cleansing agents readily dripped off the skin, these skin cleansing agents are not suitable for washing large areas such as the whole body with a lather.

Although alkyl ether carboxylic acid-based surfactants are known to be gentle to the skin, they have poor foaming properties; therefore, the use of these surfactants in combination with other surfactants such as alkyl ether sulfate is being studied (Patent Publication 3). Further, cleansing compositions containing ether carboxylic acid-based surfactants having a narrow molecular weight distribution (Patent Publications 4 and 5), a cleansing composition containing an ether carboxylic acid-based surfactant having a specific distribution of moles of ethylene oxide added (Patent Publication 6), and the like have also been proposed. However, because these cleansing compositions also produced small amounts of foam, which easily dripped off the skin, it was impossible to wash the body with a rich foam. In this way, these cleansing compositions had a problem with feeling upon application.

CITATION LIST

Patent Publication

[Patent Publication 1] JP-A-2007-112984
[Patent Publication 2] JP-A-H11-508268
[Patent Publication 3] JP-A-2008-285479
[Patent Publication 4] JP-A-S61-21199
[Patent Publication 5] JP-A-2001-207189
[Patent Publication 6] JP-A-H02-175799

SUMMARY OF THE INVENTION

The present invention provides a skin cleansing composition, comprising the following components (A) and (B):
(A) an alkyl ether carboxylic acid or a salt thereof represented by formula (1):

$$R^1-O-(CH_2CH_2O)_n-CH_2-COOM \quad (1)$$

wherein, $R^1$ represents an alkyl group having 8 to 18 carbon atoms, n represents a number of from 0 to 20, and M represents a hydrogen atom, alkali metal, alkaline earth metal, ammonium, or organic ammonium, wherein, $R^1$ has an average carbon number of from 10.8 to 12.8 and an average value of n is from 2.5 to 3.4, and wherein, the alkyl ether carboxylic acid or a salt thereof contains a component in which n=0 in an amount of from 9.9 to 27% by mass, and contains a component in which n=1 and a component in which n=2 in a total amount of less than 40% by mass, and (B) an alkyl sulfate or polyoxyethylene alkyl sulfate represented by formula (2):

$$R^2-O-(CH_2CH_2O)_m-SO_3Y \quad (2)$$

wherein, $R^2$ represents an alkyl group or an alkenyl group having 8 to 22 carbon atoms, m represents a number of from 0 to 20 and an average of m is less than 2, and Y represents a hydrogen atom or a cation selected from alkali metal, alkaline earth metal, ammonium, alkyl ammonium, alkanol ammonium, and glucammonium.

DETAILED DESCRIPTION OF THE INVENTION

The present invention relates to a skin cleansing composition capable of producing foam which does not easily drip off the skin. The skin cleansing composition lathers well and produces a large volume of foam having good foam qualities.

The present inventors found that a skin cleansing composition which lathers well and produces a large volume of foam having fine and soft foam qualities which does not easily drip off the skin can be obtained by using an alkyl ether carboxylate having a specific distribution in combination with a specific alkyl sulfate or polyoxyethylene alkyl sulfate.

Since the skin cleansing composition of the present invention lathers well and produces a large volume of foam having fine and soft foam qualities which does not easily drip off the skin, such a skin cleansing composition is also suitable for washing. Moreover, this skin cleansing composition also has excellent rinsing properties.

The alkyl ether carboxylic acid or a salt thereof of the component (A) used in the present invention is represented by formula (1).

In the formula, $R^1$ is an alkyl group having 8 to 18 carbon atoms, preferably an alkyl group having 8 to 16 carbon atoms, and more preferably an alkyl group having 10 to 16 carbon atoms. Also, although the alkyl chain of $R^1$ may be either linear or branched, from the viewpoint of foaming properties, a linear alkyl group is preferred. Also, $R^1$ has an average carbon number of from 10.8 to 12.8, preferably from 10.8 to 12.5, and more preferably from 12.1 to 12.4. It is preferable that the average carbon number be within the above range since excellent foaming properties, foam qualities, and stability at low temperature are obtained.

Also, $R^1$ preferably contains two or more alkyl groups, and the content of a component having the alkyl chain length which is contained in the highest content is preferably 55% by mass or more and less than 97% by mass, more preferably from 60 to 95% by mass, and even more preferably from 70 to 95% by mass since excellent volume of foam and foam qualities are obtained.

Also, in the formula, n represents a number of from 0 to 20, and preferably from 0 to 12. It is to be noted that n represents the number of moles of ethylene oxide added, and the average number of moles of ethylene oxide added in the composition of the component (A) (an average value of n) is from 2.5 to 3.4, preferably from 2.8 to 3.4, and more preferably from 2.8 to 3.1 since favorable foam qualities are achieved.

The alkyl ether carboxylic acid or a salt thereof of the component (A) contains, in formula (1), a component in which n=0 in an amount of from 9.9 to 27% by mass, preferably from 9.9 to 16% by mass, and more preferably from 9.9 to 15% by mass. When the content of the component in which n=0 is within the above range, the feeling of friction during rinsing is improved.

Further, the total content of a component in which n=1 and a component in which n=2 is less than 40% by mass. From the viewpoint of foam qualities and the volume of foam, the total content of components in which n=1 and 2 is preferably from 20 to 37% by mass, more preferably from 27 to 36.5% by mass, and even more preferably from 35 to 36.1% by mass.

Also, in the formula, examples of M include a hydrogen atom; alkali metal such as sodium and potassium; alkaline earth metal such as calcium and magnesium; ammonium; alkanolamine-derived ammonium such as monoethanolamine, diethanolamine, and triethanolamine. Among them, alkali metal is preferred in terms of foaming properties, stability at low temperature, and absence of coloration over time.

In formula (1), the alkyl ether carboxylic acid or a salt thereof of the component (A) preferably has a mass ratio of the components in which n=0, 1, 2, 3, and 4, (the mass of a component in which n=0):(the mass of a component in which n=1):(the mass of a component in which n=2):(the mass of a component in which n=3):(the mass of a component in which n=4), of 1:0.99 to 3.50:0.89 to 3.00:0.76 to 3.00:0.63 to 1.6 from the viewpoint that foaming properties, detergency, and a feeling of friction during rinsing can be achieved simultaneously.

Also, in formula (1), it is preferable that the content of a component in which n=0 be 9.9% by mass or more and less than 12% by mass, and a ratio of (the mass of a component in which n=0):(the mass of a component in which n=1):(the mass of a component in which n=2):(the mass of a component in which n=3):(the mass of a component in which n=4)=1:1.53 to 1.87:1.59 to 2.25:1.33 to 2.16:1.14 to 1.52, or the content of a component in which n=0 be 12% by mass or more and 17% by mass or less and a ratio of (the mass of a component in which n=0):(the mass of a component in which n=1):(the mass of a component in which n=2):(the mass of a component in which n=3):(the mass of a component in which n=4)=1:0.99 to 1.34:0.89 to 1.40:0.76 to 1.23:0.63 to 0.99 from the viewpoint of foaming properties and rinsing properties.

Further, in formula (1), it is preferable that the content of a component in which n=0 be from 9.9 to 11.5% by mass and a ratio of (the mass of a component in which n=0):(the mass of a component in which n=1):(the mass of a component in which n=2):(the mass of a component in which n=3):(the mass of a component in which n=4)=1:1.58 to 1.84:1.72 to 2.17:1.49 to 2.00:1.14 to 1.52 or, in formula (1), it is preferable that the content of a component in which n=0 be from 13 to 17% by mass and a ratio of (the mass of a component in which n=0):(the mass of a component in which n=1):(the mass of a component in which n=2):(the mass of a component in which n=3):(the mass of a component in which n=4)=1:1.00 to 1.31:0.93 to 1.34:0.79 to 1.18:0.63 to 0.99 from the viewpoint of volume of foam, foam qualities, and rinsing properties.

It is preferable that, in the component (A), in formula (1), $R^1$ be an alkyl group having 8 to 18 carbon atoms, $R^1$ have an average carbon number of from 10.8 to 12.8, and the content of a component having an alkyl chain length which is contained in the highest content be 55% by mass or more and less than 97% by mass, and further, n represent a number of from 0 to 20 and the average value thereof be from 2.5 to 3.4, and a component in which n=0 be contained in an amount of from 9.9 to 27% by mass, and a component in which n=1 and a component in which n=2 be contained in a total amount of from 20 to 37% by mass. Also, as M in the formula, a hydrogen atom, sodium, potassium, and ammonium are preferred. A cleansing composition containing the alkyl ether carboxylic acid or a salt thereof having the aforementioned configuration can achieve accelerated foaming.

It is preferable that, in the component (A), in formula (1), $R^1$ be an alkyl group having 8 to 18 carbon atoms, $R^1$ have an average carbon number of 10.8 to 12.8, and the content of a component having the alkyl chain length which is contained in the highest content be 55% by mass or more and less than 97% by mass, and further, n represent a number of from 0 to 20 and the average value thereof be from 2.5 to 3.4, and a component in which n=0 be contained in an amount of from 9.9 to 27% by mass, and a component in which n=1 and a component in which n=2 be contained in a total amount of from 27 to 36.5% by mass. Also, as M in the formula, a hydrogen atom, sodium, potassium, and ammonium are preferred. A cleansing composition containing the alkyl ether carboxylic acid or a salt thereof having the aforementioned configuration can strengthen a stop feeling during rinsing.

It is preferable that, in the component (A), in formula (1), $R^1$ be an alkyl group having 8 to 16 carbon atoms, $R^1$ have an average carbon number of 10.8 to 12.5, and the content of a component having the alkyl chain length which is contained in the highest content be from 60 to 95% by mass, and further, n represent a number of from 0 to 20 and the average value thereof be from 2.8 to 3.4, and a component in which n=0 be contained in an amount of from 9.9 to 27% by mass, preferably from 9.9 to 16% by mass, and a component in which n=1 and a component in which n=2 be contained in a total amount of from 27 to 36.5% by mass. Also, as M in the formula, a hydrogen atom, sodium, potassium, and ammonium are preferred. A cleansing composition containing the alkyl ether carboxylic acid or a salt thereof having the aforementioned configuration can have improved volume of foam and foam qualities.

It is preferable that, in the component (A), in formula (1), $R^1$ be an alkyl group having 10 to 16 carbon atoms, $R^1$ have an average carbon number of from 12.1 to 12.4, and the content of a component having the alkyl chain length which is contained in the highest content be from 60 to 95% by mass, and further, n represent a number of from 0 to 20 and the average value thereof be from 2.8 to 3.1, and a component in which n=0 be contained in an amount of from 9.9 to 15% by mass, and a component in which n=1 and a component in which n=2 be contained in a total amount of from 35 to 36.1% by mass. Also, as M in the formula, a hydrogen atom, sodium, potassium, and ammonium are preferred. A cleansing composition containing the alkyl ether carboxylic acid or a salt thereof having the aforementioned configuration can have improved volume of foam, foam qualities and less foam dripping.

It is to be noted that in the component (A) of the present invention, the distribution of the alkyl chain length of $R^1$, the average alkyl chain length of $R^1$, the amount of a component in which n=0, the average number of added moles n, and a mass ratio of the components in which n=0, 1, 2, 3, and 4 are obtained as follows from the gas chromatographic analysis of the alkyl ether carboxylic acid represented by formula (1).

[Distribution of the Alkyl Chain Length of $R^1$]

From the peak areas obtained by gas chromatography, a peak area of each alkyl chain length corresponding to n=0 mole was obtained, and setting the sum of the peak areas thus obtained at 100, the percentage of the distribution of each alkyl chain length was calculated. Similar calculation was carried out also as to n=1 to 3 moles, and the percentage values of the distribution of each alkyl chain length corresponding to n=0 to 3 moles were averaged out, whereby the distribution of the alkyl chain length of $R^1$ was obtained (from this, the alkyl group component contained in the largest amount in the composition of $R^1$ can be specified).

[Average alkyl chain length of $R^1$]

From the distribution of the alkyl chain length of $R^1$ obtained as above, the proportion of each component was obtained, which was multiplied by the number of carbon atoms of the corresponding alkyl chain length, and the resulting values were summed up. The value thus obtained was used as an average alkyl chain length.

[Amount of a Component in which n=0, Total Content of a Component in which n=1 and a Component in which n=2]

In the composition of $R^1$, the alkyl chain length which is contained in the highest content was specified, and the peak areas of the component having alkyl chain length of the highest content corresponding to n=0 to 10 were summed up by gas chromatography. By setting the total amount thus obtained at 100%, the amount of a component in which n=0, the total content of a component in which n=1 and a component in which n=2 were calculated.

[Average Number of Added Moles n]

In the composition of $R^1$, the alkyl chain length of the highest content was specified, and the peak areas of the component having the alkyl chain length of the highest content corresponding to n=0 to 10 were summed up by gas chromatography (the amount of a component in which n is 11 or more was so small that it was excluded from the calculation). By setting the total amount thus obtained at 1, each proportion of n=0 to 10 was obtained. The resulting proportion was multiplied by each number of added moles, and the sum of the resulting values was used as the average number of added moles n.

[Mass Ratio of the Components in which n=0, 1, 2, 3, and 4]

As to the ratio of each of the components having different numbers of moles of EO added, the distribution of the alkyl chain length of $R^1$ was obtained from the peak area obtained by gas chromatography using the method described above, and the component having the alkyl chain length of the highest content in the composition of $R^1$ was specified, and the ratio of each of the components having different numbers of moles of EO added was specified by the area ratio of n=0, n=1, n=2, n=3, and n=4 of the component having the alkyl chain length of the highest content.

The alkyl ether carboxylic acid or a salt thereof of the component (A) has the aforementioned composition, and from the viewpoint of less foam dripping, the content thereof is preferably 0.1% by mass or more, more preferably 0.5% by mass or more, and even more preferably 1% by mass or more and preferably 30% by mass or less, more preferably 20% by mass or less, and even more preferably 15% by mass or less of the total composition. Further, the content thereof is preferably from 0.1 to 30% by mass, more preferably from 0.5 to 20% by mass, and even more preferably from 1 to 15% by mass of the total composition.

The alkyl sulfate or polyoxyethylene alkyl sulfate of the component (B) used in the present invention is represented by the aforementioned formula (2).

In the formula, $R^2$ represents an alkyl group or an alkenyl group having 8 to 22 carbon atoms, which may be linear or branched. $R^2$ is preferably an alkyl group having 12 to 18 carbon atoms, and more preferably an alkyl group having 12 to 14 carbon atoms.

Further, in the formula, m represents a number of from 0 to 20, and more preferably from 0 to 12. The letter m represents a number of moles of ethylene oxide added, and the average number of moles added (an average value of m) of the component (B) in the composition is less than 2, and from the viewpoint of foaming properties and the volume of foam, the average value of m is preferably from 0 to 1.5.

Examples of Y include a hydrogen atom; alkali metal such as sodium and potassium; alkaline earth metal such as calcium and magnesium; ammonium, alkyl ammonium, alkanol ammonium, and glucammonium. Among them, alkali metal and ammonium are preferred in view of easy dissolution in water as well as high compatibility with water.

As the component (B), sodium lauryl sulfate, ammonium polyoxyethylene (1) lauryl ether sulfate, and the like are preferable.

Also, commercial products such as EMAL 0, EMAL 10, EMAL 125A, and EMAL 170J (all are manufactured by Kao Corporation) can be used.

The component (B) can be used alone or in combination of two or more thereof, and from the viewpoint of foaming properties and the volume of foam, the content thereof is preferably 0.1% by mass or more, more preferably 0.5% by mass or more, and even more preferably 1% by mass or more and preferably 30% by mass or less, more preferably 20% by mass or less, and even more preferably 15% by mass or less of the total composition. Further, the content thereof is preferably from 0.1 to 30% by mass, more preferably from 0.5 to 20% by mass, and even more preferably from 1 to 15% by mass of the total composition.

From the viewpoint of easy handling, the total content of the components (A) and (B) in the skin cleansing composition of the present invention is preferably 0.5% by mass or more, more preferably 1% by mass or more, and even more preferably 5% by mass or more and preferably 40% by mass or less, more preferably 30% by mass or less, and even more preferably 15% by mass or less of the total composition. Also, the content thereof is preferably from 0.5 to 40% by mass, more preferably from 1 to 30% by mass, and even more preferably from 5 to 15% by mass of the total composition.

Also, the mass ratio of the component (A) to the component (B) in the cleansing composition of the present invention is preferably (A):(B)=1:10 to 10:1, more preferably (A):(B)=1:5 to 5:1, and even more preferably (A):(B)=1:2 to 2:1. When only the component (A) is added to the cleansing composition, the foam produced using a nylon towel, lathering mesh, or the like is fine and creamy but less likely to spill out of the towel or lathering mesh. Further, the foam has a large specific gravity due to its fineness and creaminess, and due to its weight, the foam easily drips off the skin when applied to the skin. Meanwhile, when only the component (B) is added to the cleansing composition, the foam obtained relatively easily spills out of a nylon towel, lathering mesh, or the like. However, in terms of foam qualities, the foam is bubbly and watery, and when applied to the skin, it readily drips off.

The present invention can provide foam which easily spills out, in a large amount, of a nylon towel or lathering mesh (i.e., a large volume of foam), particularly when foam is produced using a nylon towel or a lathering mesh, by using a combination of the component (A) and the component (B). The foam thus obtained has fine foam qualities and does not easily drip off the skin. Thus, the cleansing composition of the present invention is suitable for washing the body, such as the face, hands, feet, and torso.

The cleansing composition of the present invention can further comprise (C) a cationic polymer, thereby further improving foaming, the volume of foam, foam qualities, and rinsing properties.

Examples of the cationic polymer include cationized cellulose, cationized starch, cationized guar gum, cationized tara gum, cationized locust bean gum, cationized fenugreek gum, cationized xanthan gum, a diallyl dialkyl quaternary ammonium salt polymer, a diallyl dialkyl quaternary ammonium salt/acrylamide copolymer, a diallyl dialkyl quaternary ammonium salt/acrylamide/acrylic acid copolymer, a vinyl imidazolium trichloride/vinylpyrrolidone copolymer, a hydroxyethylcellulose/dimethyl diallyl ammonium chloride copolymer, a vinylpyrrolidone/quaternized dimethylaminoethyl methacrylate copolymer, a polyvinylpyrrolidone/alkylamino acrylate copolymer, a polyvinylpyrrolidone/alkylamino acrylate/vinylcaprolactam copolymer, a vinylpyrrolidone/methacrylamide propyl trimethyl ammonium chloride copolymer, an alkylacrylamide/acrylate/alkylamino alkylacrylamide/polyethylene glycol methacrylate copolymer, an adipic acid/dimethylaminohydroxypropyl ethylenetriamine copolymer ("Cartaretin", product of Sandoz Inc. in the U.S.), and the cationic polymers described in JP-A-S53-139734 and JP-A-S60-36407.

Among those mentioned above, from the viewpoint of improving foam qualities and rinsing properties, cationized cellulose, cationized guar gum, a diallyl dialkyl quaternary ammonium salt polymer, a diallyl dialkyl quaternary ammonium salt/acrylamide copolymer, and a diallyl dialkyl quaternary ammonium salt/acrylamide/acrylic acid copolymer are preferable.

The component (C) can be used alone or in combination of two or more thereof, and from the viewpoint of foam qualities and rinsing properties, the content thereof is preferably 0.01% by mass or more, more preferably 0.02% by mass or more, and even more preferably 0.1% by mass or more and preferably 1% by mass or less, more preferably 0.8% by mass or less, and even more preferably 0.65% by mass or less of the total composition. Further, the content thereof is preferably from 0.01 to 1% by mass, more preferably from 0.02 to 0.8% by mass, and even more preferably from 0.1 to 0.65% by mass of the total composition.

The skin cleansing composition of the present invention can further comprise water as a solvent. Water is added as balance of the cleansing composition other than the aforementioned components and other components composing the cleansing composition. The content of water is preferably 10% by mass or more, and more preferably 15% by mass or more and preferably 94.5% by mass or less, and more preferably 90% by mass or less of the total composition.

As a favorable embodiment, the skin cleansing composition of the present invention preferably comprises the following components (A) and (B):
(A) an alkyl ether carboxylic acid or a salt thereof represented by formula (1):

$$R^1\text{—O—}(CH_2CH_2O)_n\text{—}CH_2\text{—COOM} \quad (1)$$

wherein, $R^1$ represents an alkyl group having 8 to 18 carbon atoms, n represents a number of from 0 to 20, and M represents a hydrogen atom, alkali metal, alkaline earth metal, ammonium, or organic ammonium, wherein, $R^1$ has an average carbon number of from 10.8 to 12.8, n represents a number of from 0 to 20, and an average value of n is from 2.5 to 3.4, preferably from 2.8 to 3.4, and wherein, the alkyl ether carboxylic acid or a salt thereof contains a component in which n=0 in an amount of 9.9% by mass or more and less than 12% by mass, preferably from 9.9 to 11.5% by mass, and contains a component in which n=1 and a component in which n=2 in a total amount of from 20 to 36.5% by mass, and a ratio of (the mass of a component in which n=0):(the mass of a component in which n=1):(the mass of a component in which n=2):(the mass of a component in which n=3):(the mass of a component in which n=4)=1:1.53 to 1.87:1.59 to 2.25:1.33 to 2.16:1.14 to 1.52, preferably 1:1.58 to 1.84:1.72 to 2.17:1.49 to 2.00:1.14 to 1.52, and (B) an alkyl sulfate or polyoxyethylene alkyl sulfate represented by formula (2):

$$R^2\text{—O—}(CH_2CH_2O)_m\text{—}SO_3Y \quad (2)$$

wherein, $R^2$ represents an alkyl group or an alkenyl group having 8 to 22 carbon atoms, m represents a number of from 0 to 20 and an average of m is less than 2, and Y represents a hydrogen atom or a cation selected from alkali metal, alkaline earth metal, ammonium, alkyl ammonium, alkanol ammonium, and glucammonium.

As an another preferable embodiment, the skin cleansing composition of the present invention preferably comprises the following components (A) and (B):
(A) an alkyl ether carboxylic acid or a salt thereof represented by formula (1):

$$R^1\text{—O—}(CH_2CH_2O)_n\text{—}CH_2\text{—COOM} \quad (1)$$

wherein, $R^1$ represents an alkyl group having 8 to 18 carbon atoms, n represents a number of from 0 to 20, and M represents a hydrogen atom, alkali metal, alkaline earth metal, ammonium, or organic ammonium, wherein, $R^1$ has an average carbon number of from 10.8 to 12.8, n represents a number of from 0 to 20, and an average value of n is from 2.5 to 3.4, preferably from 2.8 to 3.4, and wherein, the alkyl ether carboxylic acid or a salt thereof contains a component in which n=0 in an amount of 12% by mass or more and 17% by mass or less, preferably from 13 to 17% by mass, and contains a component in which n=1 and a component in which n=2 in a total amount of from 20 to 36.5% by mass, and a ratio of (the mass of a component in which n=0):(the mass of a component in which n=1):(the mass of a component in which n=2):(the mass of a component in which n=3):(the mass of a component in which n=4)=1:0.99 to 1.34:0.89 to 1.40:0.76 to 1.23:0.63 to 0.99, preferably 1:1.00 to 1.31:0.93 to 1.34:0.79 to 1.18:0.63 to 0.99, and (B) an alkyl sulfate or polyoxyethylene alkyl sulfate represented by formula (2):

$$R^2\text{—O—}(CH_2CH_2O)_m\text{—}SO_3Y \quad (2)$$

wherein, $R^2$ represents an alkyl group or an alkenyl group having 8 to 22 carbon atoms, m represents a number of from 0 to 20 and an average of m is less than 2, and Y represents a hydrogen atom or a cation selected from alkali metal, alkaline earth metal, ammonium, alkyl ammonium, alkanol ammonium, and glucammonium.

The skin cleansing composition of the present invention may further comprise components used in ordinary cleansers such as surfactants other than the components (A) and (B), humectants, oil components, disinfecting agents, anti-inflammatory agents, preservatives, chelating agents, thickening agents, salts, pearlescent agents, scrub agents, fragrances, cooling agents, dyes, ultraviolet absorbers, antioxidants, and plant extracts.

The skin cleansing composition of the present invention is produced by mixing the blending components using a routine method. The cleansing composition thus obtained may be either a liquid or a solid; however, when it is a liquid, the viscosity at 25° C. as measured by a B-type viscometer (manufactured by Tokyo Keiki Inc.) is preferably from 200 to 80000 mPa·s. The viscosity can be adjusted by appropriately selecting the blending components.

Also, the pH is preferably from 3 to 12, more preferably from 5 to 10.5, more preferably from 5 to 7. Also, the degree of pH is measured in each cleansing composition diluted 20-fold with ion exchange water at 25° C.

The skin cleansing composition of the present invention is suitably used as, for example, a face wash, a body soap, a hand soap, and the like. The skin cleansing composition of the present invention is preferably used as a body soap.

A method for cleansing skin by using the skin cleansing composition of the present invention is exemplified as follows. That is, a method including applying an adequate amount of the skin cleansing composition of the present invention to the body, namely the body's skin areas such as face, hands, feet, torso and the like, lathering up and washing, and then rinsing off using warm water from a shower and the like, is possible. It is also possible to apply an adequate amount of the cleansing composition of the present invention to a washing aid such as a towel, a sponge, a brush and the like, and then lather up and wash.

In connection with the aforementioned embodiments, the present invention further discloses the following compositions.

<1> A skin cleansing composition, comprising the following components (A) and (B):
(A) an alkyl ether carboxylic acid or a salt thereof represented by formula (1):

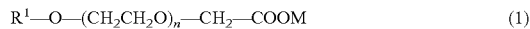

$$R^1-O-(CH_2CH_2O)_n-CH_2-COOM \quad (1)$$

wherein, $R^1$ represents an alkyl group having 8 to 18 carbon atoms, n represents a number of from 0 to 20, and M represents a hydrogen atom, alkali metal, alkaline earth metal, ammonium, or organic ammonium, wherein, $R^1$ has an average carbon number of from 10.8 to 12.8 and an average value of n is from 2.5 to 3.4, and wherein, the alkyl ether carboxylic acid or a salt thereof contains a component in which n=0 in an amount of from 9.9 to 27% by mass, and contains a component in which n=1 and a component in which n=2 in a total amount of less than 40% by mass, and
(B) an alkyl sulfate or polyoxyethylene alkyl sulfate represented by formula (2):

$$R^2-O-(CH_2CH_2O)_m-SO_3Y \quad (2)$$

wherein, $R^2$ represents an alkyl group or an alkenyl group having 8 to 22 carbon atoms, m represents a number of from 0 to 20 and an average of m is less than 2, and Y represents a hydrogen atom or a cation selected from alkali metal, alkaline earth metal, ammonium, alkyl ammonium, alkanol ammonium, and glucammonium.

<2> The skin cleansing composition according to the aforementioned <1>, wherein, in the component (A), in formula (1), a ratio of (the mass of a component in which n=0):(the mass of a component in which n=1):(the mass of a component in which n=2):(the mass of a component in which n=3):(the mass of a component in which n=4)=1:0.99 to 3.50:0.89 to 3.00:0.76 to 3.00:0.63 to 1.6.

<3> The skin cleansing composition according to the aforementioned <1> or <2>, wherein, in the component (A), in formula (1), $R^1$ contains two or more alkyl groups, and the content of a component having an alkyl chain length which is contained in the highest content is 55% by mass or more and less than 97% by mass.

<4> The skin cleansing composition according to any one of the aforementioned <1> to <3>, wherein, the component (A) comprises, in formula (1), a component in which n=0 in an amount of 9.9% by mass or more and less than 12% by mass, and a ratio of (the mass of a component in which n=0):(the mass of a component in which n=1):(the mass of a component in which n=2):(the mass of a component in which n=3):(the mass of a component in which n=4)=1:1.53 to 1.87:1.59 to 2.25:1.33 to 2.16:1.14 to 1.52, or contains a component in which n=0 in an amount of 12% by mass or more and 17% by mass or less, and a ratio of (the mass of a component in which n=0):(the mass of a component in which n=1):(the mass of a component in which n=2):(the mass of a component in which n=3):(the mass of a component in which n=4)=1:0.99 to 1.34:0.89 to 1.40:0.76 to 1.23:0.63 to 0.99.

<5> The skin cleansing composition according to any one of the aforementioned <1> to <4>, wherein the content of the component (A) is 0.1% by mass or more, preferably 0.5% by mass or more, and more preferably 1% by mass or more, and 30% by mass or less, preferably 20% by mass or less, and more preferably 15% by mass or less of a total composition.

<6> The skin cleansing composition according to the aforementioned <1>, wherein, in the component (B), in formula (2), an average number of moles of ethylene oxide added (an average value of m) is from 0 to 1.5.

<7> The skin cleansing composition according to the aforementioned <1> or <6>, wherein the content of the component (B) is 0.1% by mass or more, preferably 0.5% by mass or more, and more preferably 1% by mass or more and 30% by mass or less, preferably 20% by mass or less, and more preferably 15% by mass or less of a total composition.

<8> The skin cleansing composition according to any one of the aforementioned <1> to <7>, wherein a mass ratio of the component (A) to the component (B), (A):(B) is from 1:10 to 10:1.

<9> The skin cleansing composition according to any one of the aforementioned <1> to <7>, wherein a mass ratio of the component (A) to the component (B), (A):(B), is from 1:5 to 5:1.

<10> The skin cleansing composition according to any one of the aforementioned <1> to <7>, wherein a mass ratio of the component (A) to the component (B), (A):(B), is from 1:2 to 2:1.

<11> The skin cleansing composition according to any one of the aforementioned <1> to <10>, further comprising (C) a cationic polymer.

<12> The skin cleansing composition according to the aforementioned <11>, wherein the component (C), cationic polymer, is at least one selected from the group consisting of cationized cellulose, cationized starch, cationized guar gum, cationized tara gum, cationized locust bean gum, cationized fenugreek gum, cationized xanthan gum, a diallyl dialkyl quaternary ammonium salt polymer, a diallyl dialkyl quaternary ammonium salt/acrylamide copolymer, a diallyl dialkyl quaternary ammonium salt/acrylamide/acrylic acid copolymer, a vinyl imidazolium trichloride/vinylpyrrolidone copolymer, a hydroxyethylcellulose/dimethyl diallyl ammonium chloride copolymer, a vinylpyrrolidone/quaternized dimethylaminoethyl methacrylate copolymer, a polyvinylpyrrolidone/alkylamino acrylate copolymer, a polyvinylpyrrolidone/alkylamino acrylate/vinylcaprolactam copolymer, a vinylpyrrolidone/methacrylamide propyl trimethyl ammonium chloride copolymer, an alkylacrylamide/acrylate/alkylamino alkylacrylamide/polyethylene glycol methacrylate copolymer, and an adipic acid/dimethylaminohydroxypropyl ethylenetriamine copolymer ("Cartaretin", product of Sandoz Inc. in the U.S.).

<13> The skin cleansing composition according to the aforementioned <11>, wherein the component (C), cationic polymer, is at least one selected from the group consisting of cationized cellulose, cationized guar gum, a diallyl dialkyl quaternary ammonium salt polymer, a diallyl dialkyl quaternary ammonium salt/acrylamide copolymer, and a diallyl dialkyl quaternary ammonium salt/acrylamide/acrylic acid copolymer.

<14> The skin cleansing composition according to any one of the aforementioned <11> to <13>, wherein the content of the component (C) is 0.01% by mass or more, preferably 0.02% by mass or more, and more preferably 0.1% by mass or more and 1% by mass or less, preferably 0.8% by mass or less, and more preferably 0.65% by mass or less of a total composition.

<15> A method for cleansing skin, comprising applying the skin cleansing composition according to any one of the aforementioned <1> to <14> to a skin area, washing, and then rinsing.

EXAMPLES

The alkyl ether carboxylate of the component (A) used in the skin cleansing composition of the present invention can be produced, for example, in the following manner.

Unless otherwise noted, "%" represents % by mass. Also, the alkyl composition, the distribution of the moles of EO added, and the ratio of each component of the alkyl ether carboxylic acid in a reaction mixture produced by the reaction were measured by the following analytical method with gas chromatography (GC).

(GC Analytical Conditions)
GC instrument; the product of Agilent Technologies, 7890A
Column; the product of Agilent Technologies, DB-5
(30 m, an inner diameter of 0.25 mm, a film thickness of 0.25 μm)
Detector; FID
Carrier; helium gas, 1 mL/min
Conditions of temperature rising; temperature is raised at 5° C./min from 100° C. to 325° C., and thereafter, maintained at 325° C. for 35 minutes.

(Method of Sample Pretreatment)

Into 50 mL of methanol, 150 mg of alkyl ether carboxylate was dissolved. Also, the cleansing composition was taken in an amount of 150 mg in terms of alkyl ether carboxylate equivalent and dissolved in 50 mL of methanol. Also, when the cleansing composition contained a strong anionic surfactant such as polyoxyethylene alkyl ether sulfate, the cleansing composition was collected in such an amount that the strong anionic surfactant was 250 mg or less. From these solutions, 1 mL was taken and applied to a solid phase cartridge (manufactured by Biotage Japan Ltd., Isolute SAX, 1 g, 3 mL, 500-0100-B) which had been conditioned with 4 mL of methanol in advance, and the filtrate was received in a 10 mL round-bottom test tube. Subsequently, the filtrate was eluted with 6 mL of a solution of 4.6 g of formic acid in 100 mL of methanol, and the eluate was also collected in the same test tube. The solution thus collected was set in a block heater heated to 50° C., to which nitrogen gas was blown in, and the solution was concentrated to approximately 1 mL, which was then dried at room temperature by further blowing nitrogen gas. To the resulting product, 2 mL of a diazomethane-ether solution was added, and the resulting solution was left to stand at room temperature for 10 minutes while stirring to carry out derivatization. Subsequently, nitrogen gas was blown in at room temperature and the solution was concentrated to 500 μL or less, to which chloroform was then added to bring the total volume to 500 μL, and the resulting product was subjected to GC analysis.

It is to be noted that the diazomethane-ether solution was prepared by the following procedure using a diazomethane generator (manufactured by Miyamoto Riken Ind. Co., Ltd., GM-50). A first receiver and a second receiver, and the second receiver and a third receiver were connected using a silicone rubber plug and a Teflon (Registered trademark) tube. Into the second receiver, 0.8 g of N-methyl-N'-nitro-N-nitrosoguanidine was collected, to which 2.5 mL of ion exchange water was added. Into the third receiver, 10 mL of tert-butyl methyl ether was collected. The first, second, and third receivers were cooled on ice. Subsequently, the second receiver was equipped with a plastic syringe, into which 3 mL of a solution of 20 g of sodium hydroxide dissolved in 100 mL of ion exchange water was placed. This aqueous solution of sodium hydroxide was slowly added dropwise to generate diazomethane gas, and nitrogen gas was gently blown in from the first receiver side to dissolve the diazomethane gas in tert-butyl methyl ether in the third receiver, whereby a diazomethane-ether solution was obtained.

The following reagents were used in the aforementioned sample pretreatment.
Methanol (manufactured by Kanto Chemical Co., Inc., for high performance liquid chromatography, 25183-1B)
Formic acid (manufactured by Wako Pure Chemical Industries, Ltd., special grade chemical, 066-00461)
Chloroform (manufactured by Kanto Chemical Co., Inc., CICA first grade, 07278-01)
N-Methyl-N'-nitro-N-nitrosoguanidine (manufactured by Kanto Chemical Co., Inc., CICA first grade, 25596-51)
Tert-butyl methyl ether (manufactured by Kanto Chemical Co., Inc., CICA special grade, 04418-00)
Sodium hydroxide (manufactured by Wako Pure Chemical Industries, Ltd., special grade, 196-13761)

Production Example 1

Into a stainless-steel autoclave equipped with stirring and temperature controlling functions, 1144 g (6.14 mol) of lauryl alcohol [trade name: KALCOL 2098, manufactured by Kao Corporation], 60.2 g (0.281 mol) of myristyl alcohol [trade name: KALCOL 4098, manufactured by Kao Corporation], and 2.68 g (0.0478 mol) of potassium hydroxide were placed and dehydration was performed under reduced pressure. Subsequently, 996 g (22.6 mol) of ethylene oxide (EO) was introduced at 155° C. and reactions were allowed to proceed at a reaction temperature of 155° C. and a reaction pressure of 0.4 MPa for two hours. Upon completion of the reaction, the resulting mixture was stirred for 30 minutes at 80° C. under a reduced pressure condition of 6 kPa. Then, after removing unreacted ethylene oxide, nitrogen was introduced to normalize the pressure, and 4.82 g (0.0482 mol) of 90% lactic acid was added into the autoclave, followed by stirring at 80° C. for 30 minutes, whereby alkyl ethoxylate having 3.55 moles of EO added (hereinbelow, also referred to as "the produced AE") was obtained.

Into a glass reaction container equipped with stirring and temperature controlling functions and an oxygen gas introduction tube, 90 g (0.2 mol) of the aforementioned product, 16.7 g of a 48% aqueous solution of sodium hydroxide (0.2 mol as sodium hydroxide), 0.9 g of a palladium-platinumbismuth-based catalyst (activated carbon containing 4% of palladium, 1% of platinum, 5% of bismuth, and 50% of water), and 494.4 g of water were each placed. While stirring, the liquid temperature was raised to 70° C., and while blowing oxygen in at a ratio of 27 mol % (with respect to the produced AE/hour), catalytic oxidation reactions were carried out at a reaction temperature of 70° C. for 3.5 hours. The rate of reaction was 89%.

Upon completion of the reaction, the catalyst was filtered out from the reaction solution to provide an aqueous solution of sodium salt of alkyl ether carboxylic acid. Subsequently, 35% hydrochloric acid was added, and a liquid separation operation was performed to provide alkyl ether carboxylic acid, which will be referred to as EC1.

As a result of gas chromatography analysis, it was found that, in formula (1), M=H, $R^1$ had lauryl group/myristyl group at a ratio of 95/5, the average carbon number was 12.1, and the average value of n was 2.8, and EC1 contained a component in which n=0 in an amount of 14.7% by mass, and a component in which n=1 and a component in which n=2 in a total amount of 36.1% by mass.

Further, it was also found that the ratio of each of the components having different numbers of moles of EO added, as calculated from the measurement value of the maximum component of the composition of $R^1$, was as follows; (the mass of a component in which n=0):(the mass of a component in which n=1):(the mass of a component in which n=2):(the mass of a component in which n=3):(the mass of a component in which n=4)=1:1.22:1.23:1.06:0.83.

Production Example 2

According to Production Example 1, EO was reacted with a raw material containing a mixture of decyl alcohol [trade name: KALCOL 1098, manufactured by Kao Corporation], lauryl alcohol [trade name: KALCOL 2098, manufactured by Kao Corporation], myristyl alcohol [trade name: KALCOL 4098, manufactured by Kao Corporation], and cetyl alcohol [trade name: KALCOL 6098, manufactured by Kao Corporation] at a mass ratio of 10/70/15/5 to provide alkyl ethoxylate having 3.55 moles of EO added. In the same manner as in Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ had decyl group/lauryl group/myristyl group/palmityl group at a ratio of 10/70/15/5, the average carbon number was 12.3, and the average value of n was 3.3, and the alkyl ether carboxylic acid contained a component in which n=0 in an amount of 15.2% by mass, and a component in which n=1 and a component in which n=2 in a total amount of 31.4% by mass.

Further, it was also found that the ratio of each of the components having different numbers of moles of EO added, as calculated from the measurement value of the maximum component of the composition of $R^1$, was as follows; (the mass of a component in which n=0):(the mass of a component in which n=1):(the mass of a component in which n=2):(the mass of a component in which n=3):(the mass of a component in which n=4)=1:1.07:1.00:0.85:0.67.

Production Example 3

Into a glass reaction container equipped with stirring and temperature controlling functions, 372 g (2.00 mol) of lauryl alcohol was placed, and while stirring, the liquid temperature was raised to 70° C. Then, while adding 256 g (2.20 mol) of sodium monochloroacetate and 88 g (2.20 mol) of sodium hydroxide in divided portions, a reaction was allowed to proceed for five hours. Upon completion of the reaction, the precipitates were filtered out. Subsequently, 35% hydrochloric acid was added for acidification to obtain alkyl ether carboxylic acid (in formula (1), M=H, $R^1$ was a lauryl group, and n=0).

Production Example 4

According to Production Example 1, EO was reacted with decyl alcohol as a raw material to provide alkyl ethoxylate having 3.55 moles of EO added. In the same manner as in Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ was a decyl group, and the average value of n was 3.1, and the alkyl ether carboxylic acid contained a component in which n=0 in an amount of 16% by mass, and a component in which n=1 and a component in which n=2 in a total amount of 37% by mass.

Production Example 5

According to Production Example 1, EO was reacted with lauryl alcohol as a raw material to provide alkyl ethoxylate having 3.55 moles of EO added. In the same manner as in Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ was a lauryl group, and the average value of n was 3.1, and the alkyl ether carboxylic acid contained a component in which n=0 in an amount of 16% by mass, and a component in which n=1 and a component in which n=2 in a total amount of 37% by mass.

Production Example 6

According to Production Example 1, EO was reacted with myristyl alcohol as a raw material to provide alkyl ethoxylate having 3.55 moles of EO added. In the same manner as in Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ was a myristyl group, and the average value of n was 3.1, and the alkyl ether carboxylic acid contained a component in which n=0 in an amount of 16% by mass, and a component in which n=1 and a component in which n=2 in a total amount of 37% by mass.

Production Example 7

According to Production Example 1, EO was added to a raw material containing a mixture of lauryl alcohol and cetyl alcohol at a mass ratio of 20/80 to provide alkyl ethoxylate having 3.55 moles of EO added. In the same manner as in Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ had lauryl group/palmityl group at a ratio of 20/80, and the average value of n was 3.1, and the alkyl ether carboxylic acid contained a component in which n=0 in an amount of 16% by mass, and a component in which n=1 and a component in which n=2 in a total amount of 37% by mass.

Production Example 8

According to Production Example 1, EO was reacted with lauryl alcohol as a raw material to provide alkyl ethoxylate having 4.05 moles of EO added. In the same manner as in Production Example 1, the alkyl ethoxylate thus obtained was subjected to an oxidation reaction, and the resulting alkyl ether carboxylate was subjected to hydrochloric acid treatment, whereby alkyl ether carboxylic acid was obtained.

As a result of gas chromatography analysis, it was found that, in formula (1), M=H, $R^1$ was a lauryl group, the average value of n was 3.5, and the resulting alkyl ether carboxylic acid contained a component in which n=0 in an amount of 11.4% by mass, and a component in which n=1 and a component in which n=2 in a total amount of 30.6% by mass.

Further, it was also found that the ratio of each of the components having different numbers of moles of EO added, as calculated from the measurement value of the maximum component of the composition of $R^1$, was as follows; (the mass of a component in which n=0):(the mass of a component in which n=1):(the mass of a component in which n=2):(the mass of a component in which n=3):(the mass of a component in which n=4)=1:1.31:1.38:1.25:1.06.

Production Example 9

Into a stainless-steel autoclave equipped with stirring and temperature controlling functions, 1144 g (6.14 mol) of lauryl alcohol [trade name: KALCOL 2098, manufactured by Kao Corporation], 60.2 g (0.281 mol) of myristyl alcohol [trade name: KALCOL 4098, manufactured by Kao Corporation], and 2.6 g (0.0478 mol) of potassium hydroxide were placed and dehydration was performed under reduced pressure. Subsequently, 718 g (16.3 mol) of ethylene oxide (EO) was introduced at 155° C. and a reaction was allowed to proceed at a reaction temperature of 155° C. and a reaction pressure of 0.4 MPa for two hours. Upon completion of the reaction, the resulting mixture was cooled and then stirred for 30 minutes at 80° C. under a reduced pressure condition of 6 kPa. Then, after removing unreacted ethylene oxide, nitrogen was introduced to normalize the pressure, and 4.82 g (0.0482 mol) of 90% lactic acid was added into the autoclave, followed by stirring at 80° C. for 30 minutes, whereby alkyl ethoxylate having 2.55 moles of EO added was obtained.

Into a glass reaction container equipped with stirring and temperature controlling functions, 600 g (2.00 mol) of the aforementioned product was placed, and while stirring, the liquid temperature was raised to 70° C. Then, while adding 256 g (2.20 mol) of sodium monochloroacetate and 88 g (2.20 mol) of sodium hydroxide in divided portions, a reaction was allowed to proceed for five hours. Upon completion of the reaction, 35% hydrochloric acid was added for acidification until pH was 2.8, and the resulting oil layer was collected to obtain alkyl ether carboxylic acid, which will be referred to as EC6.

As a result of gas chromatography analysis, it was found that, in formula (1), M=H, $R^1$ had lauryl group/myristyl group at a ratio of 94/6, the average carbon number was 12.1, and the average value of n was 3.1, and EC6 contained a component in which n=0 in an amount of 9.9% by mass, and a component in which n=1 and a component in which n=2 in a total amount of 35.4% by mass.

Further, it was also found that the ratio of each of the components having different numbers of moles of EO added, as calculated from the measurement value of the maximum component of the composition of $R^1$, was as follows; (the mass of a component in which n=0):(the mass of a component in which n=1):(the mass of a component in which n=2):(the mass of a component in which n=3):(the mass of a component in which n=4)=1:1.65:1.92:1.74:1.32.

In the Examples, EC2 was obtained by mixing each of the alkyl ether carboxylic acids produced in Production Examples 5, 6, and 7 at a mass ratio of 78.75/15/6.25.

In the Examples, EC3 was obtained by mixing each of the alkyl ether carboxylic acids obtained in Production Examples 2 and 3 at a mass ratio of 90/10.

In the Examples, EC4 was obtained by mixing each of EC1 obtained in Production Example 1 and the alkyl ether carboxylic acid obtained in Production Example 4 at a mass ratio of 40/60.

In the Examples, EC5 was obtained by mixing each of the alkyl ether carboxylic acids obtained in Production Examples 2 and 8 at a mass ratio of 40/60.

Examples 1 to 35 and Comparative Examples 1 to 13

The skin cleansing compositions having the compositions as shown in Tables 3 to 5 were produced, and the volume of foam, ease of foam dripping, foam qualities, rinsing properties, and ease of washing the whole body were evaluated. The results are shown in Tables 3 to 5 altogether.

Also, the composition of the component (A) used in Examples is as shown in Tables 1 and 2.

Also, for the average numbers of moles of EO added of commercially available alkyl ether carboxylic acids used in Examples (AKYPO RLM25 (manufactured by Kao Corporation), AKYPO RLM45 (manufactured by Kao Corporation), AKYPO RLM100NV (manufactured by Kao Corporation), BEAULIGHT LCA (manufactured by Sanyo Chemical Industries, Ltd.), and ECTD-3NEX (manufactured by Nikko Chemicals, Co., Ltd)), values provided in the catalogue supplied by each vendor or values posted in the website of each vendor were referred to. Unknown alkyl composition, the amount of a component in which n=0, and the total amount of a component in which n=1 and a component in which n=2 were analyzed by the aforementioned method.

(Production Method)

The components (A) and (B) were mixed with water and homogenized while heating to 70° C. Subsequently, sodium hydroxide was added in an amount to bring pH to 6, followed by stirring to homogeneity. Further, after cooling to room temperature while stirring, other components including the component (C) were added as needed, followed by stirring to homogeneity, whereby skin cleansing compositions were obtained.

(Evaluation Method)

(1) Volume of Foam:

A lathering mesh (manufactured by Daisan Co. of Hakugen Group) was moistened with water (approximately 8 g). Then, 1 g of each skin cleansing composition was placed on the lathering mesh. The lathering mesh was held in both hands in an enveloping manner and the hands were moved in a circular motion for lathering. The hands were rubbed together in a circular motion 40 times for lathering. The foam produced with the lathering mesh was collected in a 500 mL beaker (manufactured by AGC Techno Glass Co., Ltd., 8.5 cm in diameter and 15 cm in height). After condensing the foam by shaking the beaker, the height (cm) of the foam thus collected was measured with a ruler. Then, the volume (cm$^3$) of the foam thus collected was calculated from the height thus obtained and the area of the base of the beaker.

(2) Ease of Foam Dripping:

Approximately 50 mL of the foam produced in (1) is placed on forearm wet with water (approximately 3 cm from the wrist). Subsequently, the foam-placed forearm was held up perpendicularly to the ground. After maintaining the perpendicular position for 30 seconds, the distance of dripping of the foam from the initial position was measured. This operation was repeated three times and an average value of three operations was obtained, which was used as ease of foam dripping.

(3) Foam Qualities:

One expert panelist organoleptically evaluated the foam qualities of the foam produced in (1) based on the following criteria.

5; Foam is very fine and soft.
4; Foam is slightly fine and soft.
3; Foam is soft.
2; Foam is slightly large, fragile, and slightly watery.
1; Foam is large, fragile, and watery.

(4) Rinsing Properties:

After evaluation of ease of foam dripping (2), the foam was spread over the entire forearm and rubbed 10 times in a back and forth motion to wash the arm, followed by rinsing with tap water (approximately 30° C.) At this time, the rinsing properties were organoleptically evaluated by one expert panelist based on the following criteria.

5; A slimy feel rapidly disappears, immediately followed by an appropriate feeling of friction.
4; A slimy feel slightly rapidly disappears, followed by an appropriate feeling of friction.
3; A slimy feel disappears, followed by a feeling of friction.
2; It takes some time for a slimy feel to disappear during rinsing, followed by a weak feeling of friction.
1; It took a long time for a slimy feel to disappear during rinsing, followed by a very weak feeling of friction.

(5) Ease of Washing the Whole Body:

Each skin cleansing composition (6 g) was lathered using a nylon towel and then used for washing the whole body. The "ease of washing the whole body" attributable to the volume of foam, ease of foam dripping, and foam qualities were evaluated based on the following criteria.

A; Foam difficultly drips off the skin and the whole body is very easily washed with abundant foam having soft foam qualities.
B; Foam difficultly drips off the skin and the whole body is easily washed with an appropriate amount of foam having soft foam qualities.
C; Foam does not easily spread out and the whole body is not easily washed.
D; Due to the watery, bubbly foam qualities, the foam easily drips off the skin and the whole body is not easily washed.

TABLE 1

|  | R$^1$ (% by mass) | | | | Average carbon number | Average number of moles of EO added | n = 0 Content ratio | n = 1, 2 Total amount | M (Salt) |
|---|---|---|---|---|---|---|---|---|---|
|  | C10 | C12 | C14 | C16 |  |  |  |  |  |
| EC1 | 0 | 95 | 5 | 0 | 12.1 | 2.8 | 14.7% | 36.1% | Na |
| EC2 | 0 | 80 | 15 | 5 | 12.5 | 3.1 | 16.0% | 32.5% | Na |
| EC3 | 8 | 73 | 13.5 | 4.5 | 12.2 | 2.82 | 27.0% | 27.1% | Na |
| EC4 | 60 | 38 | 2 | 0 | 10.8 | 3.2 | 12.5% | 34.8% | Na |
| EC5 | 4 | 88 | 6 | 2 | 12.1 | 3.4 | 13.3% | 31.0% | Na |
| EC6 | 0 | 94 | 6 | 0 | 12.1 | 3.1 | 9.9% | 35.4% | K |

TABLE 2

|  | R$^1$ (% by mass) | | | | Average carbon number | Average number of moles of EO added | n = 0 Content ratio | n = 1, 2 Total amount | M (Salt) |
|---|---|---|---|---|---|---|---|---|---|
|  | C10 | C12 | C14 | C16 |  |  |  |  |  |
| 25CA *1 | 0 | 68 | 26 | 6 | 12.8 | 2.5 | 16.0% | 32.5% | Na |
| 45CA *2 | 0 | 68 | 26 | 6 | 12.8 | 4.5 | 9.6% | 31.2% | Na |
| 100NV *3 | 0 | 68 | 26 | 6 | 12.8 | 10 | 4.9% | 20.4% | Na |
| LCA *4 | 0 | 100 | 0 | 0 | 12 | 3 | 2.8% | 42.8% | Na |
| Nex *5 | — | — | — | — | C13 branched | 3 | 4.2% | 40.0% | Na |

*1: AKYPO RLM25 (manufactured by Kao Corporation)
*2: AKYPO RLM45 (manufactured by Kao Corporation)
*3: AKYPO RLM100NV (manufactured by Kao Corporation)
*4: BEAULIGHT LCA (manufactured by Sanyo Chemical Industries, Ltd.)
*5: ECTD-3NEX (manufactured by Nikko Chemicals, Co., Ltd)

TABLE 3

| Component | Example | | | | | | | | | | |
|---|---|---|---|---|---|---|---|---|---|---|---|
| (% by mass) | 1 | 2 | 3 | 4 | 5 | 6 | 7 | 8 | 9 | 10 | 11 |
| A EC1 | 7.5 |  |  |  |  |  |  |  | 7.5 |  |  |
| EC2 |  | 7.5 |  |  |  |  |  |  |  |  |  |
| EC3 |  |  | 7.5 |  |  |  |  |  |  |  |  |

TABLE 3-continued

| Component (% by mass) | | | | | | | | | | | | |
|---|---|---|---|---|---|---|---|---|---|---|---|
| | EC4 | | | | 7.5 | | | | | | | |
| | EC5 | | | | | 7.5 | | | | | | |
| | EC6 | | | | | | 7.5 | | | | | |
| | 25CA *1 | | | | | | | 7.5 | | 7.5 | | |
| | 45CA *2 | | | | | | | | 7.5 | | | 7.5 |
| | 100NV *3 | | | | | | | | | | | |
| | LCA *4 | | | | | | | | | | | |
| | Nex *5 | | | | | | | | | | | |
| B | Ammonium polyoxyethylene (1) lauryl ether sulfate *6 | 7.5 | 7.5 | 7.5 | 7.5 | 7.5 | 7.5 | 7.5 | 7.5 | | | |
| | Sodium lauryl sulfate *7 | | | | | | | | | 7.5 | 7.5 | 7.5 |
| | Aqueous solution of sodium hydroxide | q.s. | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance | Balance |
| | Total | 100 | 100 | 100 | 100 | 100 | 100 | 100 | 100 | 100 | 100 | 100 |
| | pH | 6 | 6 | 6 | 6 | 6 | 6 | 6 | 6 | 6 | 6 | 6 |
| | Evaluation item: Volume of foam (cm³) | 482 | 567 | 510 | 681 | 567 | 450 | 397 | 369 | 454 | 510 | 369 |
| | Ease of foam dripping (cm) | 0.0 | 0.0 | 0.0 | 0.3 | 0.0 | 0.0 | 1.3 | 1.3 | 0.0 | 0.3 | 0.7 |
| | Foam qualities | 5.0 | 5.0 | 5.0 | 5.0 | 5.0 | 5.0 | 4.0 | 3.0 | 5.0 | 4.0 | 3.0 |
| | Rinsing properties | 5.0 | 5.0 | 5.0 | 4.0 | 5.0 | 5.0 | 3.0 | 3.0 | 5.0 | 3.0 | 3.0 |
| | Ease of washing the whole body | A | A | A | A | A | A | A | A | A | A | B |

| Component (% by mass) | | Comparative Example | | | | | | | | | | |
|---|---|---|---|---|---|---|---|---|---|---|---|---|
| | | 1 | 2 | 3 | 4 | 5 | 6 | 7 | 8 | 9 | 10 | 11 |
| A | EC1 | | | | | | | | | | | |
| | EC2 | | | | | | | | | | | |
| | EC3 | | | | | | | | | | | |
| | EC4 | | | | | | | | | | | |
| | EC5 | | | | | | | | | | | |
| | EC6 | | | | | | | | | | | |
| | 25CA *1 | 15 | | | | | | | | | | |
| | 45CA *2 | | 15 | | | | | | | | | |
| | 100NV *3 | | | 15 | | | | | | | | |
| | LCA *4 | | | | 15 | | | 7.5 | | 7.5 | | |
| | Nex *5 | | | | | 15 | | | 7.5 | | 7.5 | |
| B | Ammonium polyoxyethylene (1) lauryl ether sulfate *6 | | | | | | 15 | 7.5 | 7.5 | | | |
| | Sodium lauryl sulfate *7 | | | | | | | | | 7.5 | 7.5 | 15 |
| | Aqueous solution of sodium hydroxide | q.s. | q.s. | q.s. | q.s. | q.s. | q.s. | q.s. | q.s. | q.s. | q.s. | q.s. |
| | Purified water | Balance | Balance | Balance | Balance | Balance | Balance | Balance | Balance | Balance | Balance | Balance |
| | Total | 100 | 100 | 100 | 100 | 100 | 100 | 100 | 100 | 100 | 100 | 100 |
| | pH | 6 | 6 | 6 | 6 | 6 | 6 | 6 | 6 | 6 | 6 | 6 |
| | Evaluation item: Volume of foam (cm³) | 255 | 284 | 284 | 397 | 510 | 369 | 369 | 340 | 397 | 510 | 510 |
| | Ease of foam dripping (cm) | 1.3 | 5.7 | 6.7 | 7.3 | 8.0 | 15.0 | 5.7 | 8.3 | 6.0 | 3.0 | 3.3 |
| | Foam qualities | 3.0 | 2.0 | 2.0 | 2.0 | 1.0 | 2.0 | 3.0 | 1.0 | 3.0 | 1.0 | 2.0 |
| | Rinsing properties | 3.0 | 2.0 | 2.0 | 3.0 | 1.0 | 1.0 | 3.0 | 3.0 | 3.0 | 3.0 | 2.0 |

TABLE 3-continued

| | | | | | | | | | | |
|---|---|---|---|---|---|---|---|---|---|---|
| Ease of washing the whole body | C | D | D | D | D | D | D | D | D | D | D |

*1: AKYPO RLM25 (manufactured by Kao Corporation)
*2: AKYPO RLM45 (manufactured by Kao Corporation)
*3: AKYPO RLM100NV (manufactured by Kao Corporation)
*4: BEAULIGHT LCA (manufactured by Sanyo Chemical Industries, Ltd.)
*5: ECTD-3NEX (manufactured by Nikko Chemicals, Co., Ltd)
*6: EMAL 125A (manufactured by Kao Corporation)
*7: EMAL 10P (manufactured by Kao Corporation)

TABLE 4

| | | Example | | | | | | | |
|---|---|---|---|---|---|---|---|---|---|
| Component (% by mass) | | 12 | 13 | 14 | 15 | 16 | 17 | 18 | 19 |
| A | EC1 | 1.4 | 2.5 | 5.0 | 10.0 | 12.5 | 13.6 | 15 | 20 |
| B | Ammonium polyoxyethylene (1) lauryl ether sulfate *6 | 13.6 | 12.5 | 10.0 | 5.0 | 2.5 | 1.4 | 15 | 20 |
| | Aqueous solution of sodium hydroxide | q.s. | q.s. | q.s. | q.s. | q.s. | q.s. | q.s. | q.s. |
| | Purified water | Balance | Balance | Balance | Balance | Balance | Balance | Balance | Balance |
| | Total | 100 | 100 | 100 | 100 | 100 | 100 | 100 | 100 |
| | pH | 6 | 6 | 6 | 6 | 6 | 6 | 6 | 6 |
| | (A):(B) | 1:10 | 1:5 | 1:2 | 2:1 | 5:1 | 10:1 | 1:1 | 1:1 |
| | Evaluation item: Volume of foam (cm$^3$) | 397 | 454 | 567 | 454 | 454 | 397 | 567 | 624 |
| | Ease of foam dripping (cm) | 2.0 | 0.0 | 0.3 | 0.0 | 0.0 | 0.0 | 0.0 | 0.0 |
| | Foam qualities | 4.0 | 4.0 | 5.0 | 5.0 | 4.0 | 4.0 | 4.0 | 4.0 |
| | Rinsing properties | 3.0 | 4.0 | 4.0 | 5.0 | 5.0 | 5.0 | 5.0 | 5.0 |
| | Ease of washing the whole body | A | A | A | A | A | A | A | A |

| | | Example | | | | | Comparative Example | |
|---|---|---|---|---|---|---|---|---|
| Component (% by mass) | | 20 | 21 | 22 | 23 | 24 | 12 | 13 |
| A | EC1 | 9.0 | 1.0 | 4.5 | 0.5 | 1.5 | 3.0 | 0.0 |
| B | Ammonium polyoxyethylene (1) lauryl ether sulfate*6 | 1.0 | 9.0 | 0.5 | 4.5 | 1.5 | 0.0 | 3.0 |
| | Aqueous solution of sodium hydroxide | q.s. | q.s. | q.s. | q.s. | q.s. | q.s. | q.s. |
| | Purified water | Balance | Balance | Balance | Balance | Balance | Balance | Balance |
| | Total | 100 | 100 | 100 | 100 | 100 | 100 | 100 |
| | pH | 6 | 6 | 6 | 6 | 6 | 6 | 6 |
| | (A):(B) | 9:1 | 1:9 | 9:1 | 1:9 | 1:1 | 1:0 | 0:1 |
| | Evaluation item: Volume of foam (cm$^3$) | 397 | 397 | 397 | 397 | 284 | 255 | 284 |
| | Ease of foam dripping (cm) | 0.0 | 2.0 | 0.0 | 0.0 | 0.0 | 0.3 | 15.0 |
| | Foam qualities | 5.0 | 2.0 | 4.0 | 2.0 | 4.0 | 3.0 | 1.0 |
| | Rinsing properties | 5.0 | 3.0 | 5.0 | 3.0 | 5.0 | 5.0 | 1.0 |
| | Ease of washing the whole body | A | A | A | A | B | C | D |

*6: EMAL 125A (manufactured by Kao Corporation)

TABLE 5

| | | Example | | | | | | | | | | |
|---|---|---|---|---|---|---|---|---|---|---|---|---|
| Component (% by mass) | | 25 | 26 | 27 | 28 | 29 | 30 | 31 | 32 | 33 | 34 | 35 |
| A | EC1 | 3.0 | 3.0 | | 3.0 | 3.0 | 3.0 | 3.0 | 3.0 | 3.0 | 3.0 | 3.0 |
| | EC6 | | | 3.0 | | | | | | | | |

TABLE 5-continued

|  | Component (% by mass) | Example |  |  |  |  |  |  |  |  |  |  |
|---|---|---|---|---|---|---|---|---|---|---|---|---|
|  |  | 25 | 26 | 27 | 28 | 29 | 30 | 31 | 32 | 33 | 34 | 35 |
| B | Ammonium polyoxyethylene (1) lauryl ether sulfate *6 | 3.0 | 3.0 | 3.0 | 3.0 | 3.0 | 3.0 | 3.0 | 3.0 | 3.0 | 3.0 | 3.0 |
| C | Polyquaternium-7 *9 |  |  |  | 3.0 |  |  |  |  |  |  |  |
|  | Polyquaternium-39 *10 |  |  |  |  | 0.5 |  |  |  |  |  |  |
|  | Polyquaternium-6 *11 |  |  |  |  |  | 1.5 |  |  |  |  |  |
|  | Polyquaternium-22 *12 |  |  |  |  |  |  |  | 0.9 |  |  |  |
|  | Polyquaternium-22 *13 |  |  |  |  |  |  |  |  | 2.0 |  |  |
|  | Guar hydroxypropyltrimonium chloride *14 |  | 0.1 | 0.1 |  |  |  |  |  |  | 0.01 | 0.02 |
|  | Cationized cellulose *15 |  |  |  |  |  |  |  |  | 1.0 |  |  |
|  | Aqueous solution of sodium hydroxide | q.s. | q.s. | q.s. | q.s. | q.s. | q.s. | q.s. | q.s. | q.s. | q.s. | q.s. |
|  | Purified water | Balance | Balance | Balance | Balance | Balance | Balance | Balance | Balance | Balance | Balance | Balance |
|  | Total | 100 | 100 | 100 | 100 | 100 | 100 | 100 | 100 | 100 | 100 | 100 |
|  | pH | 6 | 6 | 6 | 6 | 6 | 6 | 6 | 6 | 6 | 6 | 6 |
|  | Evaluation item: Volume of foam (cm$^3$) | 400 | 420 | 430 | 500 | 450 | 454 | 430 | 420 | 420 | 400 | 410 |
|  | Ease of foam dripping (cm) | 0.0 | 0.0 | 0.0 | 0.0 | 0.0 | 0.0 | 0.0 | 0.0 | 0.0 | 0.0 | 0.0 |
|  | Foam qualities | 4.0 | 4.5 | 4.0 | 5.0 | 5.0 | 5.0 | 5.0 | 5.0 | 5.0 | 4.5 | 4.5 |
|  | Rinsing properties | 4.0 | 5.0 | 4.5 | 5.0 | 5.0 | 5.0 | 5.0 | 5.0 | 5.0 | 4.0 | 4.5 |
|  | Ease of washing the whole body | A | A | A | A | A | A | A | A | A | A | A |

*6: EMAL 125A (manufactured by Kao Corporation)
*9: MERQUAT550 (manufactured by Nalco Company) Content of active ingredient 9%
*10: MERQUAT3331 (manufactured by Nalco Company) Content of active ingredient 10%
*11: MERQUAT100 (manufactured by Nalco Company) Content of active ingredient 41%
*12: MERQUAT295 (manufactured by Nalco Company) Content of active ingredient 38%
*13: MERQUAT280 (manufactured by Nalco Company) Content of active ingredient 40%
*14: JAGUAR C17-K (manufactured by Rhodia) Content of active ingredient 100%
*15: POIZ C-60H (manufactured by Kao Corporation) Content of active ingredient 100%

The invention claimed is:

1. A skin cleansing composition, comprising components (A) and (B):
   (A) an alkyl ether carboxylic acid or a salt thereof represented by formula (1):

$$R^1\text{—}O\text{—}(CH_2CH_2O)_n\text{—}CH_2\text{—}COOM \quad (1)$$

wherein, $R^1$ represents an alkyl group having 10 to 16 carbon atoms, n represents a number of from 0 to 20, and M represents a hydrogen atom, alkali metal, alkaline earth metal, ammonium, or organic ammonium,
   wherein, $R^1$ has an average carbon number of from 10.8 to 12.8 and an average value of n is from 2.8 to 3.4,
   and wherein, the alkyl ether carboxylic acid or a salt thereof contains a component in which n=0 in an amount of from 9.9 to 27% by mass, and contains a component in which n=1 and a component in which n=2 in a total amount of 20% by mass or more and less than 40% by mass, and
   (B) an alkyl sulfate or polyoxyethylene alkyl sulfate represented by formula (2):

$$R^2\text{—}O\text{—}(CH_2CH_2O)_m\text{—}SO_3Y \quad (2)$$

wherein, $R^2$ represents an alkyl group or an alkenyl group having 8 to 22 carbon atoms, m represents a number of from 0 to 20 and an average of m is less than 2, and Y represents a hydrogen atom or a cation selected from alkali metal, alkaline earth metal, ammonium, alkyl ammonium, alkanol ammonium, and glucammonium.

2. The skin cleansing composition according to claim 1, wherein, in the component (A), in the formula (1), $R^1$ represents an alkyl group having 10 to 16 carbon atoms, the average value of n is from 2.8 to 3.4, and the total content of a component in which n=1 and a component in which n=2 is from 27 to 36.5% by mass.

3. The skin cleansing composition according to claim 1, wherein, in the component (A), in the formula (1), (the mass of a component in which n=0):(the mass of a component in which n=1):(the mass of a component in which n=2):(the mass of a component in which n=3):(the mass of a component in which n=4)=1:0.99 to 3.50:0.89 to 3.00:0.76 to 3.00:0.63 to 1.6.

4. The skin cleansing composition according to claim 1, wherein, in the component (A), in the formula (1), $R^1$ contains two or more alkyl groups, and the content of a component having an alkyl chain length which is contained in the highest content is 55% by mass or more and less than 97% by mass.

5. The skin cleansing composition according to claim 1, which comprises a component in which n=0 in an amount of 9.9% by mass or more and less than 12% by mass and has a ratio of (the mass of a component in which n=0):(the mass of a component in which n=1):(the mass of a component in which n=2):(the mass of a component in which n=3):(the mass of a component in which n=4) of 1:1.53 to 1.87:1.59 to 2.25:1.33 to 2.16:1.14 to 1.52, or comprises a component in which n=0 in an amount of 12% by mass or more and 17% by mass or less and has a ratio of (the mass of a component in which n=0):(the mass of a component in which n=1):(the mass of a component in which n=2):(the mass of a component in which n=3):(the mass of a component in which n=4) of 1:0.99 to 1.34:0.89 to 1.40:0.76 to 1.23:0.63 to 0.99, in the component (A), in the formula (1).

6. The skin cleansing composition according to claim 1, wherein a mass ratio of the component (A) to the component (B), (A):(B), is from 1:10 to 10:1.

7. The skin cleansing composition according to claim 1, wherein a mass ratio of the component (A) to the component (B), (A):(B), is from 1:5 to 5:1.

8. The skin cleansing composition according to claim 1, wherein a mass ratio of the component (A) to the component (B), (A):(B), is from 1:2 to 2:1.

9. The skin cleansing composition according to claim 1, further comprising (C) a cationic polymer.

10. The skin cleansing composition according to claim 9, wherein the content of the component (C) is from 0.01 to 1% by mass of a total composition.

* * * * *